(12) United States Patent
Watson, Jr. et al.

(10) Patent No.: US 6,271,042 B1
(45) Date of Patent: Aug. 7, 2001

(54) BIOCHIP DETECTION SYSTEM

(75) Inventors: Robert Malcolm Watson, Jr., San Leandro; Haseeb R. Chaudhry, Berkeley; James S. Lee, Castro Valley, all of CA (US)

(73) Assignee: Alpha Innotech Corporation, San Leandro, CA (US)

( * ) Notice: Subject to any disclaimer, the term of this patent is extended or adjusted under 35 U.S.C. 154(b) by 0 days.

(21) Appl. No.: 09/140,164

(22) Filed: Aug. 26, 1998

(51) Int. Cl.⁷ ................................................. G01N 21/64
(52) U.S. Cl. ................. 436/172; 250/458.1; 250/459.1; 422/82.08
(58) Field of Search .................................. 422/52, 82.07, 422/82.08; 436/172; 250/361 C, 458.1, 459.1

(56) References Cited

U.S. PATENT DOCUMENTS

| | | | |
|---|---|---|---|
| 4,415,732 | 11/1983 | Caruthers et al. | 536/27 |
| 4,458,066 | 7/1984 | Caruthers et al. | 536/27 |
| 4,537,861 | * 8/1985 | Elings et al. | 436/518 |
| 4,816,513 | 3/1989 | Bridgham et al. | 525/54.11 |
| 5,047,524 | 9/1991 | Andrus et al. | 536/27 |
| 5,053,454 | 10/1991 | Judd | 525/54.11 |
| 5,091,652 | * 2/1992 | Mathies et al. | 250/458.1 |
| 5,093,268 | 3/1992 | Leventis et al. | 436/172 |
| 5,096,807 | * 3/1992 | Leaback | 435/6 |
| 5,112,736 | 5/1992 | Caldwell et al. | 435/6 |
| 5,132,418 | 7/1992 | Caruthers et al. | 536/27 |
| 5,192,980 | * 3/1993 | Dixon et al. | 356/326 |
| 5,239,484 | 8/1993 | Hayashi et al. | 364/500 |
| 5,262,530 | 11/1993 | Andrus et al. | 536/25.31 |
| 5,297,288 | 3/1994 | Hemminger et al. | 395/700 |
| 5,324,483 | 6/1994 | Cody et al. | 422/131 |
| 5,324,633 | 6/1994 | Fodor et al. | 435/6 |
| 5,356,776 | 10/1994 | Kambara et al. | 435/6 |
| 5,395,594 | 3/1995 | Nokihara et al. | 422/135 |
| 5,427,930 | 6/1995 | Birkenmeyer et al. | 435/91.52 |
| 5,453,247 | 9/1995 | Beavis et al. | 422/68.1 |

(List continued on next page.)

FOREIGN PATENT DOCUMENTS

| | | | |
|---|---|---|---|
| 0640828 | * 3/1995 | (EP) . | |
| WO 96/27025 | 9/1996 | (WO) | C12Q/1/68 |
| WO 97/12030 | 4/1997 | (WO) | C12M/1/40 |
| WO 97/45730 | 12/1997 | (WO) | G01N/33/50 |
| WO 99/00520 | 1/1999 | (WO) | C12Q/1/68 |
| WO 99/27140 | 6/1999 | (WO) | C12Q/1/68 |

OTHER PUBLICATIONS

"Fast Forward; Genome Dread," Stephen S. Hall, Jan. 18, 1998, The New York Times Archives.

"Multiplexed biochemical assays with biological chips," Stephen Fodor et al., Nature 364; pp. 555–556, 1993.

"Microarrays: biotechnology's discovery platform for functional genomics," Mark Schena et al., Elsevier Science Ltd., Tibtech Jul. 1998, vol. 16, pp. 301–306.

(List continued on next page.)

Primary Examiner—Jeffrey Snay
(74) Attorney, Agent, or Firm—Haverstock & Owens LLP

(57) ABSTRACT

A biochip detection system detects and locates samples that are labeled with multiple fluorescent tags and are located on a biochip. This biochip detection system includes a charge coupled device (CCD) sensor, a broad spectrum light source, a lens, a light source filter, and a sensor filter. The CCD sensor comprises two dimensional CCD arrays to simultaneously detect light waves from at least a substantial portion of the biochip. The broad spectrum light source is optically coupled to the CCD sensor and is configured to be utilized with a variety of different fluorescent tags which have differing excitation wavelengths.

17 Claims, 6 Drawing Sheets

U.S. PATENT DOCUMENTS

| | | |
|---|---|---|
| 5,468,606 | 11/1995 | Bogart et al. .............................. 435/5 |
| 5,472,672 | 12/1995 | Brennan ................................ 422/131 |
| 5,510,270 | 4/1996 | Fodor et al. ........................... 436/518 |
| 5,512,490 * | 4/1996 | Walt et al. ............................. 436/171 |
| 5,522,272 | 6/1996 | Vecere et al. ...................... 73/864.62 |
| 5,529,756 | 6/1996 | Brennan ................................ 422/131 |
| 5,541,113 | 7/1996 | Siddigi et al. .......................... 436/56 |
| 5,545,531 * | 8/1996 | Rava et al. ............................... 435/6 |
| 5,547,839 | 8/1996 | Dower et al. ............................ 435/6 |
| 5,563,033 | 10/1996 | Lawrence et al. ....................... 435/6 |
| 5,571,639 | 11/1996 | Hubbell et al. .......................... 430/5 |
| 5,585,639 | 12/1996 | Dorsel et al. ..................... 250/458.1 |
| 5,593,839 | 1/1997 | Hubbell et al. .......................... 435/6 |
| 5,597,694 | 1/1997 | Munroe et al. .......................... 435/6 |
| 5,605,662 | 2/1997 | Heller et al. ......................... 422/68.1 |
| 5,631,734 * | 5/1997 | Stern et al. ........................... 356/317 |
| 5,632,957 | 5/1997 | Heller et al. ......................... 422/68.1 |
| 5,633,365 | 5/1997 | Stokke et al. ..................... 536/24.31 |
| 5,635,402 * | 6/1997 | Alfano et al. ........................... 436/63 |
| 5,639,428 | 6/1997 | Cottingham .......................... 422/112 |
| 5,645,114 | 7/1997 | Bogen et al. ........................ 141/145 |
| 5,645,801 | 7/1997 | Bouma et al. ...................... 422/68.1 |
| 5,653,939 | 8/1997 | Hollis et al. ............................ 422/50 |
| 5,690,894 | 11/1997 | Pinkel et al. ........................ 422/68.1 |
| 5,707,797 | 1/1998 | Windle ..................................... 435/6 |
| 5,720,923 | 2/1998 | Haff et al. ............................ 422/68.1 |
| 5,720,928 | 2/1998 | Schwartz .............................. 422/186 |
| 5,736,257 | 4/1998 | Conrad et al. .................... 428/474.4 |
| 5,736,333 | 4/1998 | Livak et al. .............................. 435/6 |
| 5,744,305 | 4/1998 | Fodor et al. .............................. 435/6 |
| 6,087,102 | 7/2000 | Chenchik et al. ....................... 435/6 |

OTHER PUBLICATIONS

L.E. Sindelar and J.M. Jaklevic, "High–Throughput DNA Synthesis in a Multichannel Format," Human Genome Center and Engineering Research and Development Department, Engineering Division, Lawrence Berkeley Laboratory, University of California, Berkeley, California 94720, pp. 1 to 8.

Robert L. Letsinger and V. Mahadevan, "Stepwise Synthesis of Oligodeoxyribonucleotides on an Insoluble Polymer Support," J Am Chem Soc, vol. 88:22, pp. 5319–5324, Nov. 20, 1966.

* cited by examiner

BIOCHIP DETECTION SYSTEM

FIELD OF THE INVENTION

The invention relates to the field of detectors for analysis of biological samples located on biochips. More particularly, the invention relates to the field of detectors that analyze samples labeled with a tag while utilizing a charge coupled device sensor.

BACKGROUND OF THE INVENTION

Detection devices that detect and locate samples contained on a biochip via laser light sources and laser scanners are well known in the art. These detection devices require that the samples be labeled by a fluorescent tag. Typically, these detection devices rely on laser light sources to excite the samples that are labeled by a fluorescent tag and causes biologically active samples to output emitted light waves. The laser source is scanned to serially excite each sample on the biochip to detect any emitted light waves from the samples that are biologically active.

Unfortunately, these detection devices utilizing either the laser light source or the laser scanner suffer from various drawbacks. First, laser scanners utilized to detect the emitted light waves from the exited samples on the biochip typically require wait times upwards of five minutes for sufficient resolution. Because laser scanners operate as a serial scanning device by sequentially detecting one sample at a time on the surface of the biochip, laser scanners are inherently inefficient at detecting the emitted light waves from an array of samples.

Further, laser light sources utilized within the detection devices inherently only emit coherent light waves which span over an extremely narrow range of wavelengths. Fluorescent tags are generally responsive to a single frequency of light or light from a narrow frequency band. Thus, the use of the laser light sources severely limits the flexibility of those detection devices because only one type of fluorescent tag can be used. To use other tags, additional laser sources must be used. Further, to evaluate a biochip that has been treated with multiple tags, the prior art's long duration scan cycle must be performed for each one of the required laser sources.

For example, if samples on a biochip were labeled with two different fluorescent tags and the different tags required light waves with substantially different excitation wavelengths, analyzing these samples would require the user to change laser light sources the analysis of all the samples were completed. Additionally, to be able to handle samples labeled with different fluorescent tags with differing excitation wavelengths, the user is required to have access to a variety of laser light sources. Since laser light sources are costly and specialized items, there are substantial costs and inconveniences associated with utilizing these prior detection devices.

Therefore, it is desirable to have an ability to detect and locate samples labeled with multiple tags contained on a biochip, without the need for a laser light source. It is also desirable have an ability to detect and locate samples labeled with a tag contained on a biochip, without the need for a serial scanning device.

SUMMARY OF THE INVENTION

The invention is a biochip detection system for detecting and locating samples that are labeled with multiple tags and are located on a biochip. This biochip detection system includes a charge coupled device (CCD) sensor, a broad spectrum light source, a lens, a light source filter, and a sensor filter. The CCD sensor comprises two dimensional CCD arrays to simultaneously detect light waves from at least a substantial portion of the biochip. The broad spectrum light source is optically coupled to the CCD sensor and is configured to be utilized with a variety of different fluorescent tags which have differing excitation wavelengths.

The light source filter is optically coupled between the light source and the biochip and is configured to only substantially allow light waves that have an excitation wavelength corresponding to a particular fluorescent tag to reach the biochip. The light source filter prevents light waves that have similar wavelengths to an emission wavelength of the particular fluorescent tag from reaching the biochip or the CCD sensor. The sensor filter is optically coupled between the biochip and the CCD sensor and is configured to only substantially allow light waves that have the emission wavelength corresponding to the fluorescent tag to reach the CCD sensor. The sensor filter prevents extraneous light waves from giving the CCD sensor false signals.

The lens and the CCD sensor are optimized and matched to each other such that the sensor operates at or below the diffraction rating of the lens. Further, the resolution of the CCD sensor is matched to the samples on the biochip such that the CCD sensor oversamples each of the samples a sufficient number of times. Additionally, the lens is configured to frame at least a substantial portion of the biochip.

The biochip detection system is optimized to provide a higher dynamic range, increased sensitivity, and faster throughput compared to system utilizing laser scanners. Further, the biochip detection system is capable of utilizing a same broad spectrum light source to excite samples labeled with a variety of fluorescent tags.

DETAILED DESCRIPTION OF THE PREFERRED EMBODIMENT

Figure 1:
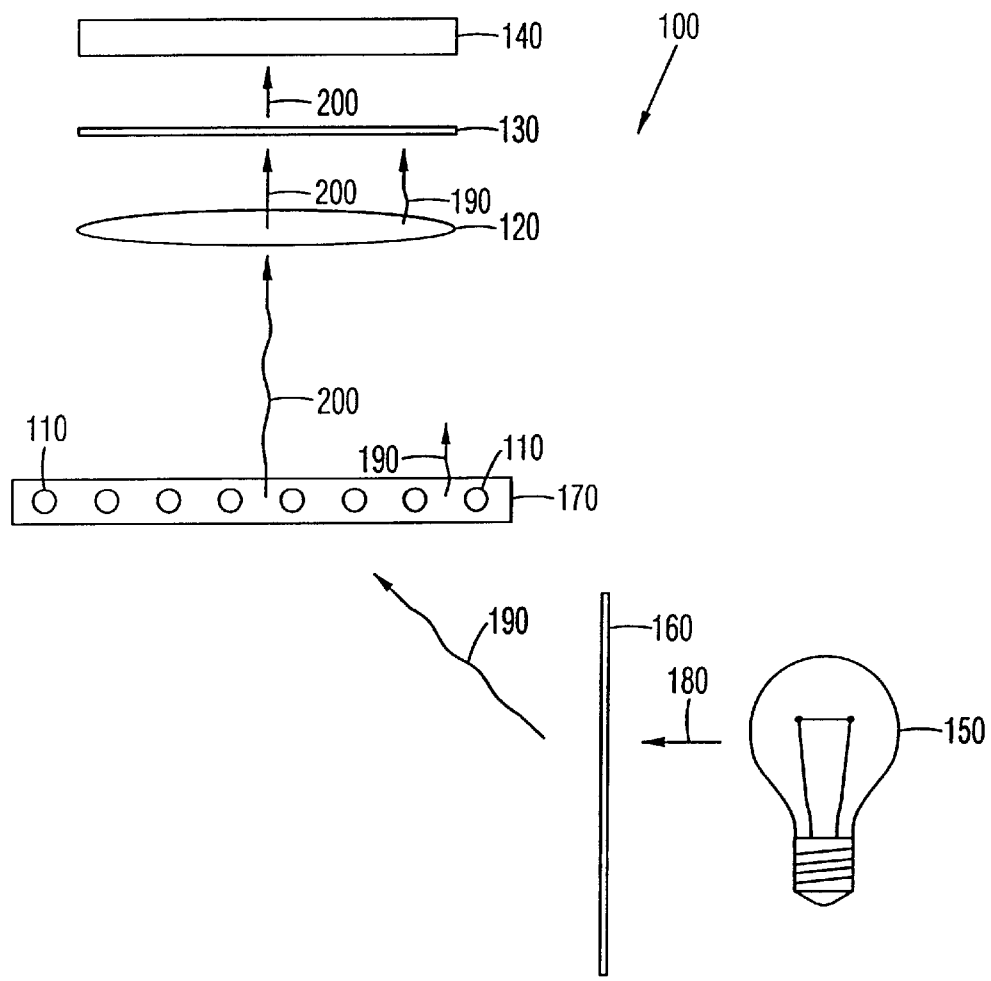
FIG. 1 illustrates a schematic side view of internal elements of the preferred embodiment of the present invention.

FIG. 1 illustrates a side view of the preferred embodiment of the present invention. This preferred embodiment is a biochip detection system 100 as shown in FIG. 1. The biochip detection system 100 preferably includes a lens 120, a sensor filter 130, a charge coupled device (CCD) sensor 140, a light source 150, and a light source filter 160. Preferably, the biochip detection system 100 is configured to detect and locate samples 110 within a biochip 170. The samples 110 and the biochip 170 are shown for exemplary purposes only and are not intended to be part of the present invention. For the purposes of this specification, the biochip 170 is configured to have an array of samples 110 arranged in a predetermined number of rows and columns on top of a substrate. Further, the samples 110 contained within the biochip 170 are capable of including DNA or other biological material. For the biochip detection system 100 to properly operate, the samples 110 are labeled with a tag. The biochip 170 in the preferred embodiment is configured to hold samples 110 which are labeled with multiple tags. However, it will be apparent to those skilled in the art to utilize samples 110 only labeled by one tag on the biochip 170. The samples 110 in the preferred embodiment are labeled with a fluorescent tag. However, it will be apparent to those skilled in the art to substitute this fluorescent tag with a chemiluminescent tag, colormetric tag, or the like. The process of labeling samples with a tag is well known in the art.

The biochip detection system 100 detects and locates which ones of the plurality of samples 110 are fluorescently labeled within the biochip 170. The biochip detection system 100 operates by exciting the samples 110 labeled by a fluorescent tag with light waves having an excitation wavelength thereby generating samples 110 that emit light waves having an emitted wavelength. Next, the CCD sensor 140 simultaneously detects the light waves having the emitted wavelength from at least a portion of the biochip 170. Specific elements and procedures of the biochip detection system 100 are described in detail below.

The CCD sensor 140 is preferably configured to include a two dimensional array of charge coupled devices. Preferably by having the CCD sensor 140 as a two dimensional sensor, the biochip detection system 100 is capable of simultaneously imaging either an entire area or a portion of the biochip 170 (depending on the size of the biochip 170) for light waves emitted by the samples 110. By simultaneously imaging all the biochip 170, the CCD sensor 140 allows the biochip detection system 100 to complete the detection process in most cases well under one minute and in some cases in twenty-five seconds. In an alternate embodiment, the CCD sensor 140 comprises cooled charge coupled devices. By having the charge coupled devices within the CCD sensor 140 cooled, background noise is reduced and signal clarity is maximized. In this preferred embodiment, the CCD sensor 140 is manufactured by Sony Corporation having the model number ICX 038DLA. It will be apparent to those skilled in the art to utilize a different CCD sensor 140.

The light source 150 is preferably a broad spectrum bulb that is configured to output light waves over a wide range of wavelengths. Preferably, the light source 150 is optically coupled to the biochip 170. Because the light source 150 generates light waves over a wide range of wavelengths, the light source 150 is capable of forming light waves to excite samples labeled with a wide variety of fluorescent tags. In this preferred embodiment, the light source 150 is manufactured by General Electric Corporation having the model number 150 Watt EKE. It will be apparent to those skilled in the art to select a different light source.

The lens 120 is preferably a compound lens that includes multiple lens elements. The lens 120 is located in an optical path between the biochip 170 and the CCD sensor 140. Preferably, the lens 120 transmits light waves emitted from the samples 110 to the CCD sensor 140. The lens 120 is capable of adjusting and optimizing a magnification parameter such that a desired portion of the biochip 170 is captured by the CCD sensor 140 with an appropriate field of view. Preferably, the lens 120 is configured such that the CCD sensor 140 operates at or below the diffraction limit of the lens 120. In this preferred embodiment, the lens 120 is manufactured by Fujinon having a focal length of 25 millimeters and f-stop of 1:0.85. It will be apparent to those skilled in the art that the lens 120 can be substituted for a different lens or multiple lenses.

Preferably, the light source filter 160 is optically coupled between the light source 150 and the biochip 170. The light source filter 160 is preferably configured to substantially only allow light waves generated by the light source 150 with a predetermined excitation wavelength to reach the biochip 170. The predetermined excitation wavelength corresponds to a particular wavelength that excites one of the samples 110 that is labeled with a particular fluorescent tag. The predetermined excitation wavelength depends on the sample in conjunction with the fluorescent tag. In other words, the light source filter 160 substantially blocks all light waves from the light source 150 with wavelengths other than the predetermined excitation wavelength from reaching the biochip 170. By blocking substantially all light waves that have wavelengths other than the predetermined excitation wavelength, the light source filter 160 prevents erroneous light waves generated by the light source 150 from giving the CCD sensor 140 erroneous signals.

Preferably, the sensor filter 130 is optically coupled between the CCD sensor 140 and the biochip 170. As shown in FIG. 1, the sensor filter 130 is preferably between the CCD sensor 140 and the lens 120. By placing the sensor filter 130 between the lens 120 and the CCD sensor 140, the chances of distorting the light waves for detection by the CCD sensor 140 is minimized. Nevertheless, it will be apparent to those skilled in the art that the sensor filter 130 also can be configured between the lens 120 and the biochip 170. The sensor filter 130 is preferably configured to substantially only allow light waves that are emitted from a sample labeled with a particular fluorescent tag that has a predetermined emitted wavelength to reach the CCD sensor 140. The predetermined emitted wavelength occurs during excitation of this sample and depends on the sample in conjunction with the particular fluorescent tag. Preferably, the sensor filter 130 is optimized to parameters of the light source 150 and prevents extraneous light waves from reaching the CCD sensor 140 thereby increasing the accuracy and sensitivity of the biochip detection system 100. It will be apparent to those of ordinary skill in the art that the filter selection is made to correspond with the fluorescent tags and also the sample type.

The biochip detection system 100 is capable of efficiently detecting and locating samples 110 on the biochip 170. The CCD sensor 140 and the lens 120 are preferably optimized relative to each other and also to the samples 110 on the biochip 170. In particular, the CCD sensor 140 preferably has a transmission resolution to oversample each of the samples 110 by eight to nine times. For example, the CCD sensor 140 is preferably configured to have each of the samples 110 be optically detected by eight to nine pixels. Additionally, the lens 120 is preferably optimized to allow the CCD sensor 140 to operate at or below the diffraction limit of the lens 120.

In operation, the biochip detection system 100 is preferably configured to analyze the biochip 170. The samples 110 are contained within the biochip 170 and are labeled with a multiple fluorescent tags. The biochip detection system 100 initiates operation by activating the light source 150. The light waves emitted from the light source 150 are represented with a light wave 180 in FIG. 1. Next, the light wave 180 preferably passes through the light source filter 160. As the light wave 180 passes through the filter, some wavelengths of the light wave 180 are blocked. A resultant light wave after passage through the light source filter 160 is represented as a light wave 190 as shown in FIG. 1. Preferably, the light wave 190 only substantially includes light waves with a predetermined excitation wavelength which correspondingly excites the samples 110 which are labeled with the particular fluorescent tag.

As the samples 110 are excited by the predetermined excitation wavelength in the light wave 190, the samples 110 produce light waves which are represented by a light wave 200 as shown in FIG. 1. The light wave 200 preferably includes light waves with a predetermined emission wavelength which are produced by the samples 110. The light wave 200 then passes through the lens 120. Some extraneous light waves with the predetermined excitation wavelength also pass through the lens 120 as shown by the light wave 190. Next, the sensor filter 130 preferably blocks out substantially all light waves with wavelengths other than the predetermined emission wavelength; the sensor filter 130 substantially only allows light waves represented by the light wave 200 to reach the CCD sensor 140. By substantially allowing only light waves having the predetermined emission wavelength to reach the CCD sensor 140, the CCD sensor 140 is capable of accurately detecting and locating the samples 110 on the biochip 170. As a result, the CCD sensor 140 is prevented from erroneously detecting stray light waves.

The biochip detection system 100 is capable of accommodating a variety of fluorescent tags without switching the light source 150, the lens 120, or the CCD sensor 140. To utilize multiple fluorescent tags with the biochip detection system 100, only the light source filter 160 and the emission filter 130 are preferably changed. By merely changing the light source filter 160 and the sensor filter 130, the biochip detection system 100 is capable of detecting and locating the samples labeled by this new fluorescent tag. Preferably, the light source filter 160 is changed such that substantially only light waves with an excitation wavelength corresponding to a new fluorescent tag reach the samples labeled by this new fluorescent tag. Further, the sensor filter 130 is preferably changed such that substantially only light waves with an emission wavelength corresponding to the new fluorescent tag reach the CCD sensor 140.

Figure 2:
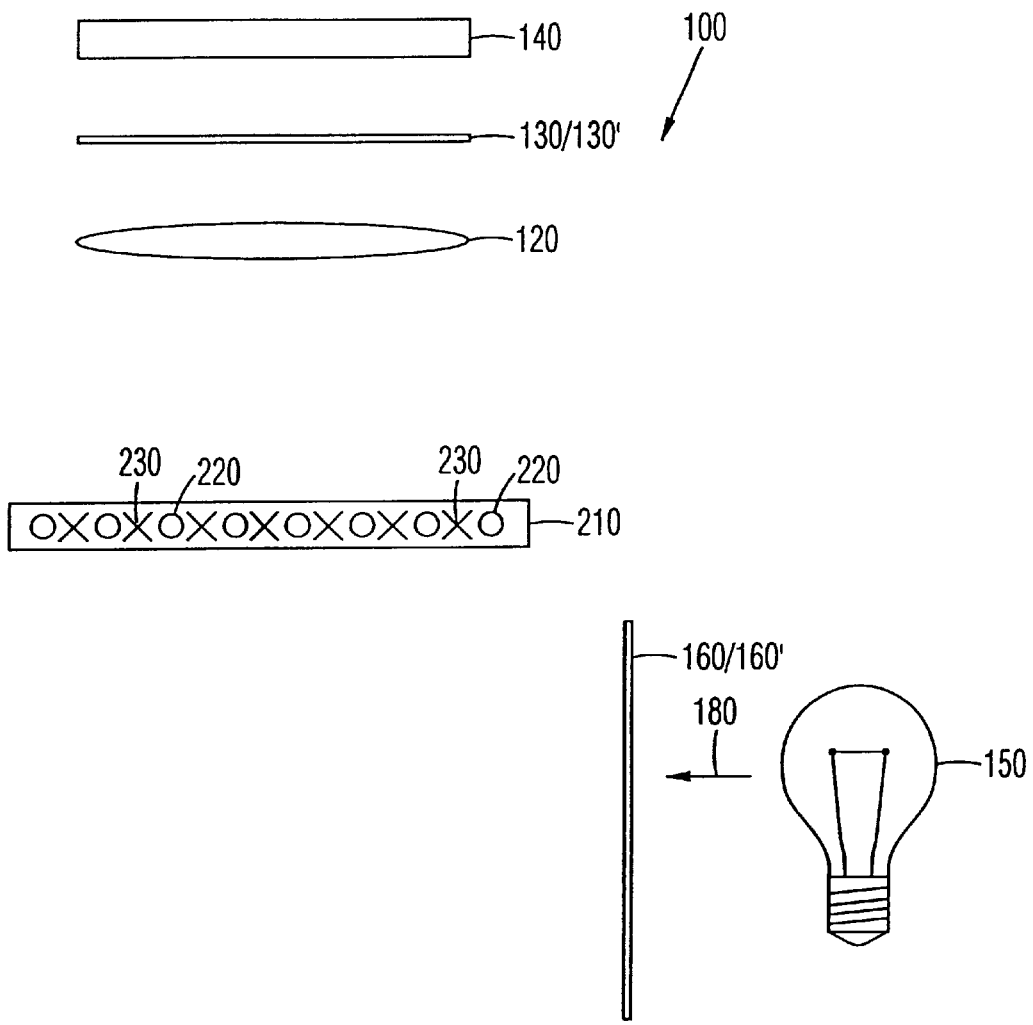
FIG. 2 illustrates a schematic side view of the preferred embodiment configured to analyze two sets of samples on a single biochip with each set of samples labeled with a different fluorescent tag.

FIG. 2 illustrates the biochip detection system 100 configured to analyze a biochip 210 having two sets of samples with each set of samples labeled by a different fluorescent tag. The configuration of the biochip detection system 100 which includes the light source 150, the lens 120, the sensor filters 130 and 130', the light source filters 160 and 160', and the CCD sensor 140 is similar to the biochip detection system 100 in FIG. 1. The sensor filters 130 and 130' are used interchangeably, one each for detecting the presence of different fluorescent tags. The light source filters 160 and 160' are used interchangeably to illuminate the biochip 210 with different wavelengths of light. It will be apparent to those skilled in the art that additional filters can be utilized. The biochip 210 contains a first set of samples 220 which is labeled by a first fluorescent tag, and a second set of samples 230 which is labeled by a second fluorescent tag. First, the biochip detection system 100 is configured to locate and detect the first set of samples 220. For proper configuration to detect and locate the first set of samples 220, the source light filter 160 preferably substantially only allows light waves with an excitation wavelength corresponding to the first fluorescent tag to reach the biochip 210. Further, the sensor filter 130 preferably substantially only allows light waves with an emission wavelength corresponding to the first fluorescent tag to reach the CCD sensor 140.

After the biochip detection system 100 is finished detecting and locating the first set of samples 220, the system 100 is configured to detect and locate the second set of samples 230. For proper configuration to detect and locate the second set of samples 230, the source light filter 160' preferably substantially only allows light waves with an excitation wavelength corresponding to the second fluorescent tag to reach the biochip 210. Further, the sensor filter 130' preferably substantially only allows light waves with an emission wavelength corresponding to the second fluorescent tag to reach the CCD sensor 140. The filter can be manually changed. For systems used to routinely tests samples labeled with several known fluorescent tags, the filters can be automatically interchanged, for example, using a so-called "jukebox". Although the first set of samples 220 and the second set of samples 230 are described as being labeled with a fluorescent tag, it will be apparent to those skilled in the art to substitute a fluorescent tag with a chemiluminescent tag, colormetric tag, and the like.

Figure 3:
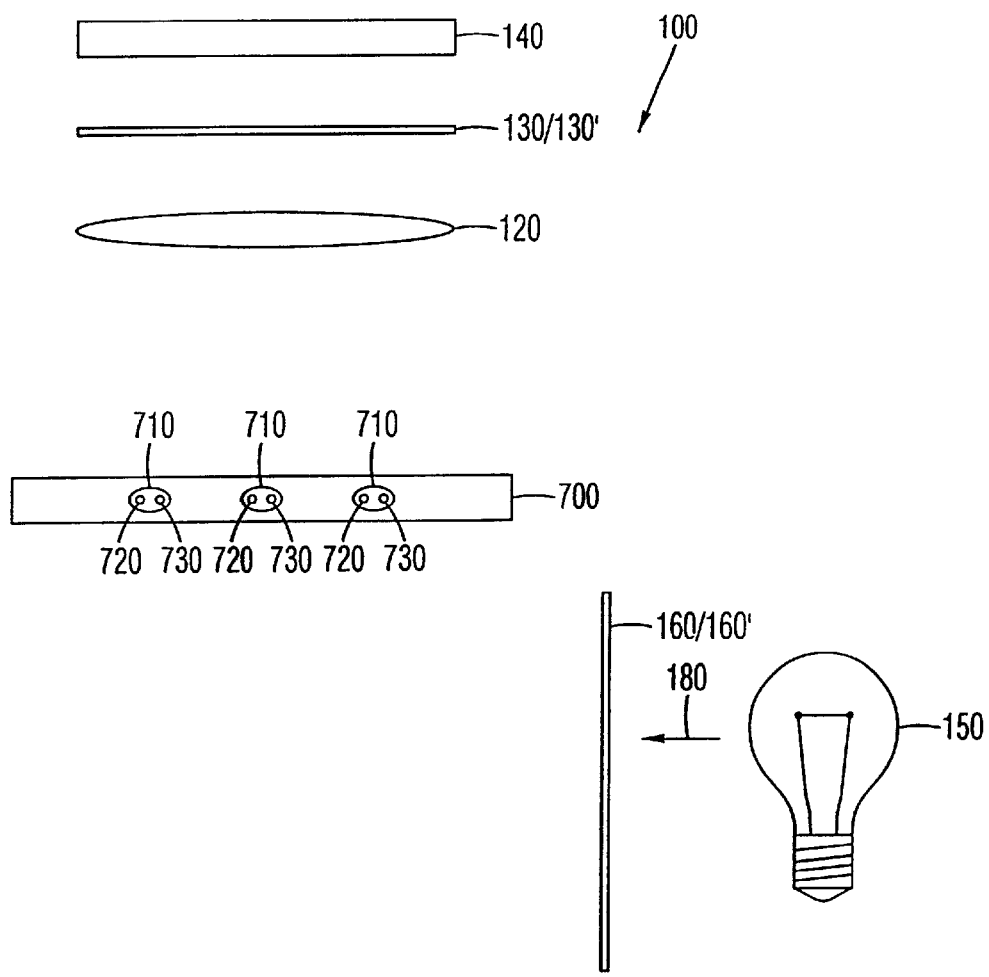
FIG. 3 illustrates a schematic side view of the preferred embodiment configured to analyze a plurality of samples on a single biochip with the plurality of samples labeled with multiple fluorescent tags.

FIG. 3 illustrates the biochip detection system 100 configured to analyze a biochip 700 having a plurality of samples 710 wherein each of the plurality of samples 710 are preferably labeled by multiple fluorescent tags. The configuration of the biochip detection system 100 which includes the light source 150, the lens 120, the sensor filters 130 and 130', the light source filters 160 and 160', and the CCD sensor 140 remain identical to the biochip detection system 100 in FIG. 2. The sensor filters 130 and 130' are used interchangeably, one each for detecting the presence of different fluorescent tags. The light source filters 160 and 160' are used interchangeably to illuminate the biochip 700 with different wavelengths of light. It will be apparent to those skilled in the art that additional filters can be utilized. The plurality of samples 710 are represented as being labeled by a first fluorescent tag 720 and a second fluorescent tag 730. It will be apparent to those with ordinary skill in the art to label the plurality of samples 710 with any number of tags.

First, the biochip detection system 100 is configured to locate and detect the plurality of samples 710 that are labeled with the first fluorescent tag 720. For proper configuration to detect and locate the plurality of samples 710 that are labeled with the first fluorescent tag 720, the source light filter 160 preferably substantially only allows light waves with an excitation wavelength corresponding to the first fluorescent tag to reach the biochip 700. Further, the sensor filter 130 preferably substantially only allows light waves with an emission wavelength corresponding to the first fluorescent tag 720 to reach the CCD sensor 140.

After the biochip detection system 100 is finished detecting and locating the plurality of samples 710 that are labeled with the first fluorescent tag 720, the system 100 is configured to detect and locate the plurality of samples 710 that are labeled with the second fluorescent tag 730. For proper configuration to detect and locate the plurality of samples 710 that are labeled with the second fluorescent tag 730, the source light filter 160' preferably substantially only allows light waves with an excitation wavelength corresponding to the second fluorescent tag 730 to reach the biochip 700.

Further, the sensor filter 130' preferably substantially only allows light waves with an emission wavelength corresponding to the second fluorescent tag 730 to reach the CCD sensor 140. The filter can be manually changed. For systems used to routinely tests samples labeled with several known fluorescent tags, the filters can be automatically interchanged, for example, using a so-called "jukebox". Although the plurality of samples 710 are described as being labeled with multiple fluorescent tags, it will be apparent to those skilled in the art to substitute multiple fluorescent tags with multiple chemiluminescent tags, colormetric tags, and the like.

Figure 4:
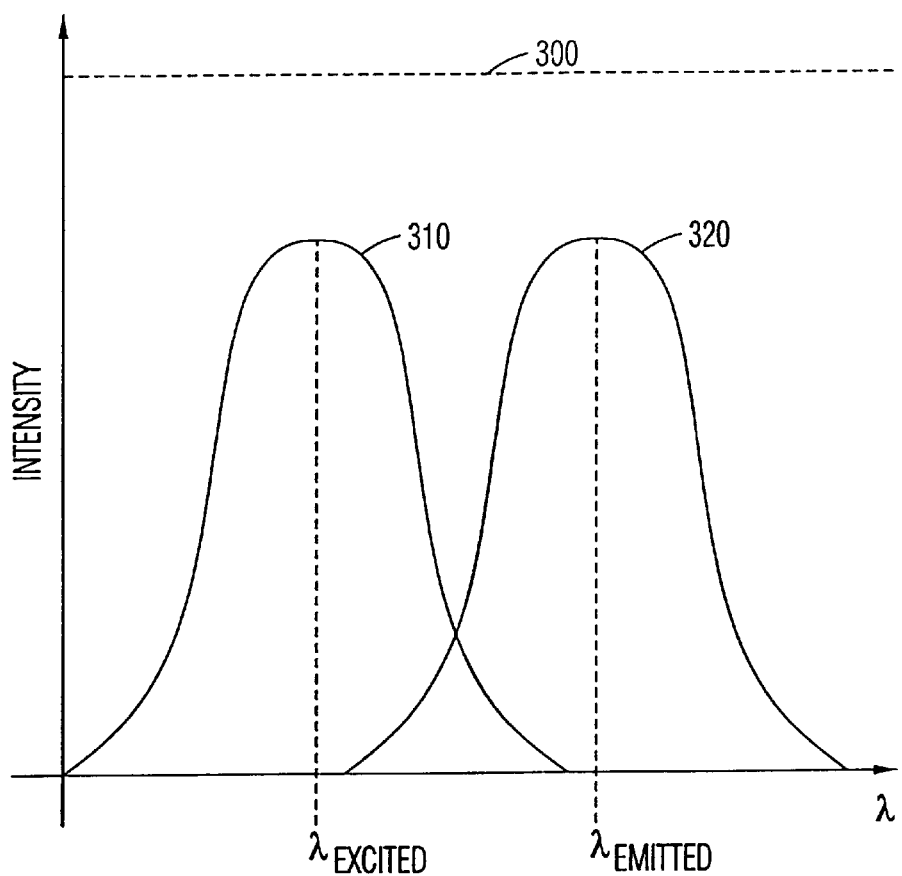
FIG. 4 is a graph that illustrates a relationship between a light intensity versus a wavelength of an excitation light of a particular fluorescent tag, an emitted light of this particular fluorescent tag, and the source light as utilized in the present invention.

FIG. 4 illustrates a graph representing intensity of light along the vertical axis and wavelength along the horizontal axis. A curve 300 is representative of the light output from the light source 150 (FIGS. 1, 2, and 3). As observed from the curve 300, the light source 150 outputs light waves preferably at an uniform intensity over a range of wavelengths. A curve 310 is centered around $\lambda_{Exicited}$ and represents a desired light intensity and wavelength to strike a sample labeled with a particular fluorescent tag in order to excite this sample. A curve 320 is centered around $\lambda_{Excited}$ and represents an emitted light intensity and wavelength from this sample while this sample is excited by light waves represented by the curve 310.

The curves 300, 310, and 320 illustrate the functions of the light source filter 160 and the sensor filter 130 as illustrated in FIGS. 1, 2, and 3 and as described above. For example, while in operation, the light source 150 preferably outputs light waves represented by the curve 300. Preferably, the light source filter 160 substantially only allows light waves that have wavelengths centered around the $\lambda_{Excited}$ to reach the sample labeled by this particular fluorescent tag. Consequently, these light waves that have wavelengths centered around the $\lambda_{Excited}$ excite the sample and are represented by the curve 310. While excited, this sample preferably emits light waves that have wavelengths centered around the $\lambda_{Emitted}$. Preferably, the sensor filter 130 substantially only allows light waves that have wavelengths centered around the $\lambda_{Emitted}$ (which are represented by the curve 320) to reach the CCD sensor 140.

By having the source light filter 160 prevent light waves that have wavelengths centered around the $\lambda_{Emitted}$ from striking this sample, the source light filter 160 prevents erroneous light waves from passing through the sensor filter 130 and striking the CCD sensor 140. Further, by having the sensor filter 130 prevent light waves that have wavelengths centered around the $\lambda_{Excited}$ from passing through the biochip 170 and then striking the CCD sensor 140, the sensor filter 130 prevents erroneous readings from the CCD sensor 140. As a result of the source light filter 160 and the sensor filter 130, fewer or no stray, erroneous light waves strike the CCD sensor 140.

Figure 5:
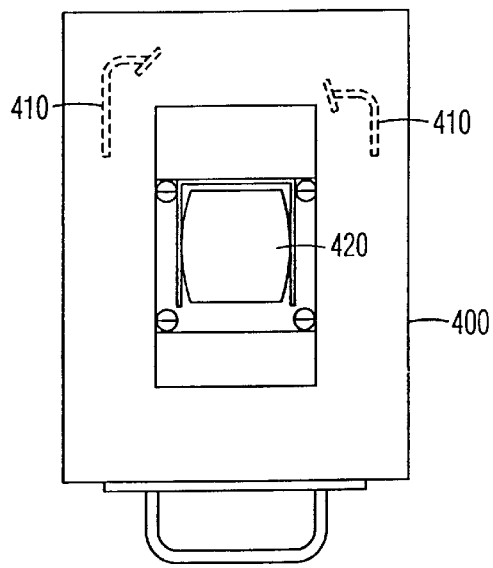
FIG. 5 illustrates a top view of an external housing of an alternate embodiment.

FIG. 5 illustrates an external top view of an alternate embodiment of the biochip detection system 100. A main housing 400 is configured to hold the biochip 170 and the light source 150. The main housing 400 is also configured to be light proof. By being light proof, the main housing 400 prevents extraneous light waves from giving the CCD sensor 140 erroneous signals. At least one articulating mirror 410 is utilized within the main housing 400 for appropriately directing light waves from the light source 150 to the biochip 170. A camera housing 420 is utilized to hold the CCD sensor 140 and coupled to the main housing 400.

Figure 6:
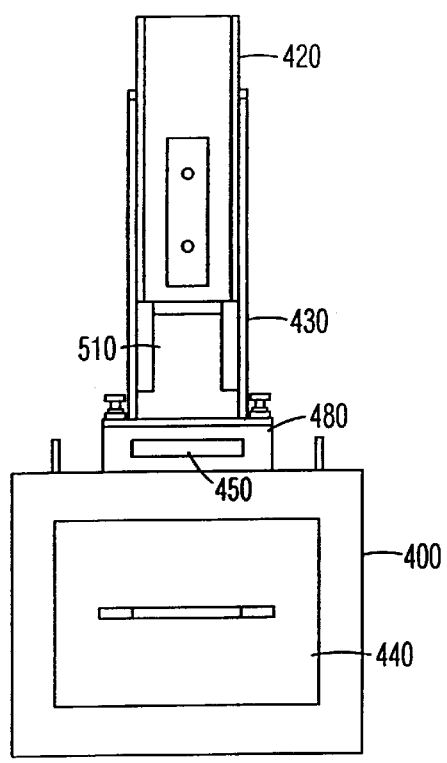
FIG. 6 illustrates a side view of the external housing of the alternate embodiment.

FIG. 6 illustrates an external side view of the alternate embodiment of the biochip detection system 100. The main housing 400 includes a drawer 440 which allows a user to change the biochip 170, adjust the light source filter 160, and/or adjust the light source 150. The drawer 440 includes appropriate seals to engage the main housing 400 such that the main housing 400 remains light proof. A filter box 480 is coupled to the main housing 400. The filter box 480 is configured to securely hold the sensor filter 130 and has an opening 450 to accept the sensor filter 130. The camera housing 420 is mounted to the filter box 480 via a camera mounting bracket 430. Preferably, a light shield 510 is mounted between the camera housing 420 and the filter box 480 to prevent stray light waves from entering either the camera housing 420, the main housing 400, or the filter box 480.

Figure 7:
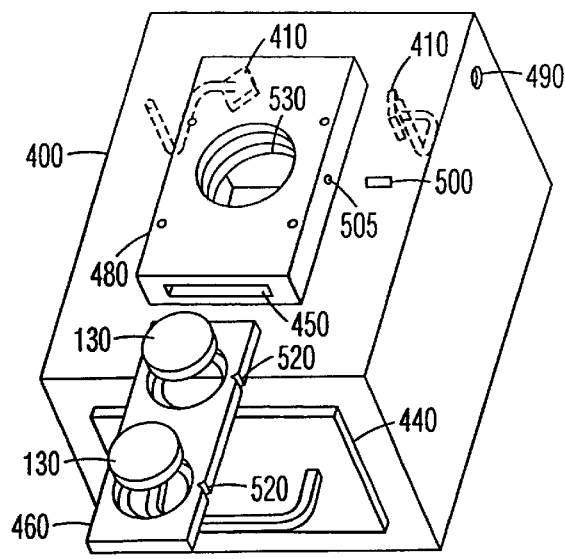
FIG. 7 illustrates a perspective view of the external housing of the alternate embodiment.

FIG. 7 illustrates an external perspective view of the alternate embodiment of the biochip detection system 100. For the sake of clarity, the camera housing 420, the camera mounting bracket 430, and the light shield 510 are omitted from FIG. 6. A fiber optic port 490 is provided in the main housing 400. The fiber optic port 490 allows the biochip detection system 100 to interface with an external light source which is capable of transmitting light via a fiber optic cable connected to the external light and the fiber optic port 490. The filter box 480 has a light channel 530 for allowing light to pass through the filter box 480 from the main housing 400 to the camera housing 420. Further, the filter box 480 also has an opening 505 to accept a ball plunger 500. A filter holder 460 is configured to hold at least one sensor filter 130 and has a plurality of notches 520. The filter holder 460 is configured to slide through the opening 450 in the filter box 480. The ball plunger 500 is configured to engage one of the plurality of notches 520 to appropriately position the filter holder 460 relative to the filter box 480.

Figure 8:
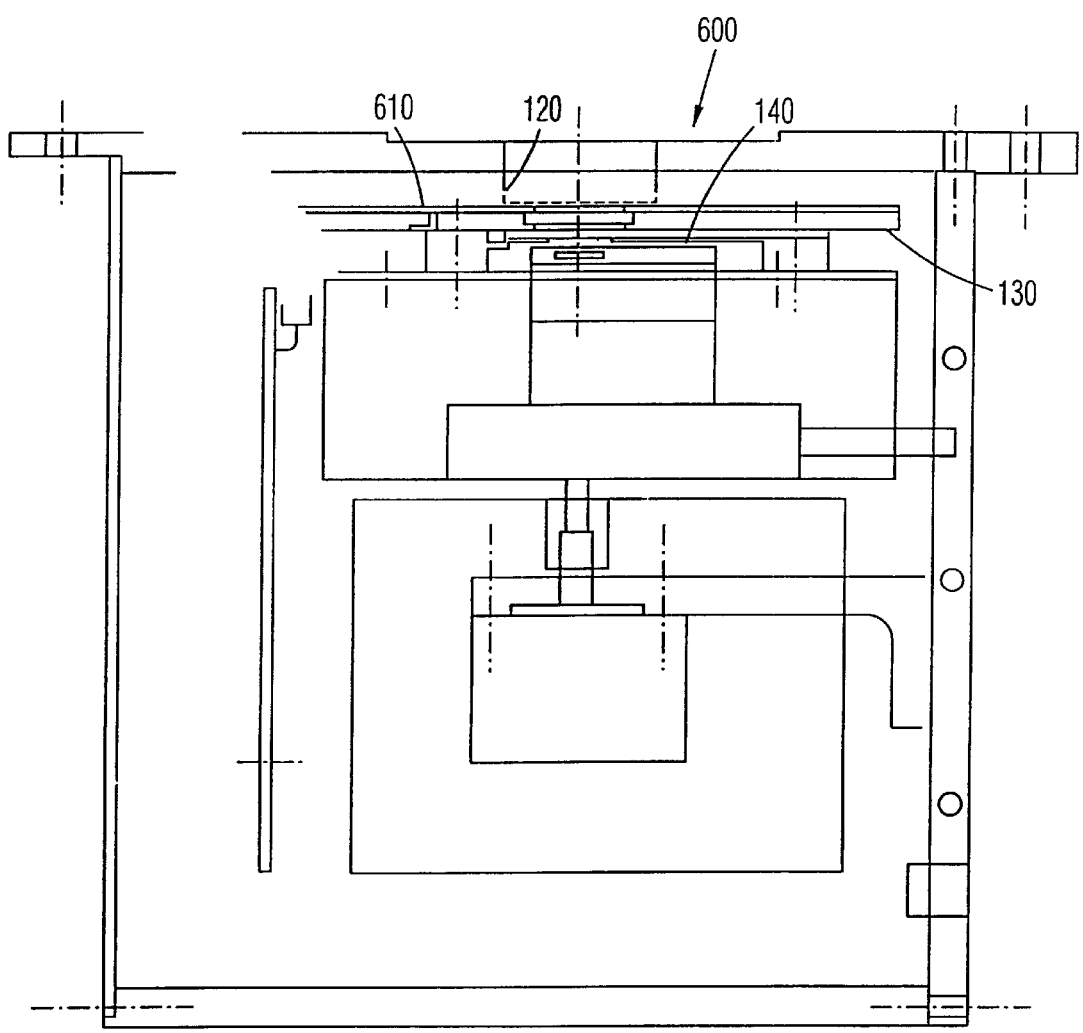
FIG. 8 illustrates a side view of a camera housing of the preferred embodiment.

A preferred embodiment of the external housing is similar to the alternate embodiment as shown in FIGS. 5, 6, and 7. A main difference between the alternate embodiment and the preferred embodiment is that the preferred embodiment does not utilize the filter box 480 and the filter holder 460 as shown in FIGS. 5, 6, and 7. Instead, the preferred embodiment of the external housing preferably couples the camera mount bracket 430 directly to the main housing 400. Further, the camera housing 420 as shown in FIGS. 5 and 6 is modified and replaced in the preferred embodiment by a camera housing 600. The camera housing 600 is illustrated in FIG. 8. Unlike the alternate embodiment of the camera housing 420 (FIGS. 5 and 6), the camera housing 600 preferably contains a filter wheel 610 which holds at least one sensor filter 130. Preferably, the filter wheel 610 optically couples the sensor filter 130 between the lens 120 and the CCD sensor 140. Further, the filter wheel 610 is preferably configured to change positions thus allowing different sensor filters 130 to be optically coupled between the lens 120 and the CCD sensor 140.

The present invention has been described in terms of specific embodiments incorporating details to facilitate the understanding of the principles of construction and operation of the invention. Such reference herein to specific embodiments and details thereof is not intended to limit the scope of the claims appended hereto. It will be apparent to those skilled in the art that modifications can be made in the embodiments chosen for illustration without departing from the spirit and scope of the invention.

Specifically, it will be apparent to one of ordinary skill in the art that the device of the present invention could be implemented in several different ways and the apparatus disclosed above is only illustrative of the preferred embodiment of the invention and is in no way a limitation. For example, it would be within the scope of the invention to vary the dimensions disclosed herein. In addition, it will be apparent that the various aspects of the above-described invention can be utilized singly or in combination with one or more of the other aspects of the invention described herein. In addition, the various elements of the present invention could be substituted with other elements.

What is claimed is:

1. An apparatus comprising:
   a. a biochip configured for supporting an array of samples;
   b. a sensor configured for detecting emitted light from the array of sample;
   c. a single source board spectrum light source optically coupled to the sensor configured to illuminate the array of samples on the biochip with an excitation light having a first excitation wavelength and a second excitation wavelength;
   d. a matched filter optically coupled between the array of samples and the single source board spectrum light source for selecting between the first excitation wavelength and the second excitation wavelength to pass therethrough and strike the array of samples; and
   e. a matched filter optically coupled between the sample and the sensor for selecting between emitted light having a first emission wavelength and a second emission wavelength to pass therethrough and strike the sensor, the a first emission wavelength and a second emission wavelength resulting from the first excitation wavelength and the second excitation wavelength striking the array of samples, respectively.

2. The apparatus according to claim 1 wherein the sensor is a charge coupled device.

3. The apparatus according to claim 1 wherein the sensor is a two dimensional charge coupled device.

4. The apparatus according to claim 1, further comprising a lens optically coupled between the array of samples on a biochip and the sensor for focusing the emitted light.

5. The apparatus according to claim 4, wherein the lense has a focal length of approximately 25 millimeters and an f-stop value of 1:0.85.

6. An apparatus comprising
   a. a biochip configured to support a two-dimensional array of tag labeled samples;
   b. a two dimensional CCD sensor for detecting emitted light from the tag labeled sample on the biochip; and
   c. a lens optically coupled between the two dimensional CCD sensor and the biochip and configured to transmit the emitted light to the two dimensional CCD sensor wherein the lens has a focal length of approximately 25 millimeters and an f-stop value of 1:0.85 and is configured to be within two inches of the tag labeled sample.

7. The apparatus according to claim 6, further comprising a sensor filter optically coupled between the two dimensional CCD sensor and the lens wherein the sensor filter is configured to only substantially allow light waves emitted from the two dimensional array of tag labeled samples on the biochip to reach the CCD sensor.

8. The apparatus according to claim 6, further comprising a light source to illuminate the two dimensional array of tag labeled samples on a biochip.

9. The apparatus according to claim 8, wherein the light source is a single source broad spectrum light source.

10. The apparatus according to claim 8, further comprising a light source filter configured to be optically coupled between the light source and the tag labeled sample on a biochip wherein the light source filter is configured to only substantially allow light waves having an excitation wavelength corresponding to the tag labeled samples to reach the two dimensional array of tag labeled samples on a biochip.

11. A system configured to detect and locate fluorescently labeled samples, the system comprising:
   a. a biochip configured to hold the fluorescently labeled samples;
   b. a light source configured to simultaneously illuminate all the fluorescently labeled samples on the biochip;
   c. a two dimensional CCD sensor optically coupled to the light source and configured for concurrently detecting and locating emitted light from the fluorescently labeled samples on the biochip; and
   d. a lens having a focal length of approximately 25 millimeters and an f-stop value of 1:0.85 optically coupled between the light source and the two dimensional CCD sensor and configured to appropriately magnify the biochip onto the two dimensional CCD sensor.

12. A system configured to detect and locate a first set of samples labeled by a first fluorescent tag emitting a first emission wavelength and a second set of samples labeled by a second fluorescent tag emitting a second emission wavelength, the first and second set of samples, the system comprising:
   a. a biochip for supporting the first and the second set of samples in a two dimensional array;
   b. a light source configured to selectively illuminate all the flourescently labeled samples on the biochip at a first excitation wavelength and a second excitation wave length;
   c. a two dimensional CCD sensor optically coupled to the light source and configured for concurrently detecting and locating the first emmision wavelength from the first set of samples and the second emmision wavelength from the second set of samples;
   d. a lens optically coupled between the light source and the two dimensional CCD sensor and configured to transmit the first emmision wavelength and the second emmision wavelength to the two dimensional CCD sensor;
   e. a first light source filter for selectively transmitting the first excitation wave wavelength to the to the first set of samples;
   f. a first sensor filter selectively and optically coupled to the two dimensional CCD sensor and configured for substantially only transmitting the first emmision wavelength to the two dimensional CCD sensor;
   g. a second light source filter for selectively transmitting the first excitation wave wavelength to the to the second set of samples; and
   h. a second sensor filter selectively and optically coupled to the two dimensional CCD sensor and configured for substantially only transmitting the second emission wavelength to the two dimensional CCD sensor.

13. A method of detecting and locating a first sample labeled by a first fluorescent tag and a second sample labeled by a second fluorescent tag, the method comprising the following steps:
   a. placing the first sample and the second sample on a biochip;
   b. selectively exciting the first sample on the biochip by substantially directing only light having a first excitation wavelength for exciting the first fluorescent tag from a broad spectrum light source to the first sample;

c. selectively detecting the first sample during the step of exciting the first sample by substantially directing only light having a first emission wavelength emitted by and from the first sample to a two dimensional CCD sensor;

d. selectively exciting the second sample on the biochip by substantially directing only light having a second excitation wavelength for exciting the second fluorescent tag from the broad spectrum light source to the second sample; and e. selectively detecting the second sample during the step of exciting the second sample by substantially directing only light having a second emission wavelength emitted by and from the second sample to the two dimensional CCD sensor.

14. A method of detecting and locating samples labeled with a fluorescent tag, the method comprising the following steps:

a. arranging the samples in an array on a biochip;

b. simultaneously illuminating the array of samples with a light source;

c. focusing an emitted light from the sample via a lens wherein the lens has a focal length of approximately 25 millimeters and an f-stop value of 1:0.85 and is located at a distance that is less than 6.0 inches from the sample;

d. simultaneously detecting the emitted light from the samples labeled with the fluorescent tag via a CCD sensor.

15. The method according to claim 14, further comprising inserting a light source filter adjacent to the light source wherein the light source filter is configured to substantially block light waves that have wavelengths outside an excitation wavelength range of the fluorescent tag from reaching the array of samples on the biochip.

16. The method according to claim 14 further comprising inserting a sensor filter adjacent to the CCD sensor wherein the sensor filter is configured to substantially block light waves that have wavelengths outside an emission wavelength range of the fluorescent tag from reaching the CCD sensor.

17. The method according to claim 14 wherein the CCD sensor comprises a two dimensional array of charge coupled devices.

* * * * *